United States Patent [19]
Miyaguchi

[11] Patent Number: 5,882,292
[45] Date of Patent: Mar. 16, 1999

[54] MAGNETIC THERAPEUTIC SHEET AND A METHOD OF MAKING THE SAME

[76] Inventor: Naoki Miyaguchi, 201 Parerowaiyaru Funatsu II, 1-6-4, Minatogoten, Wakayama-shi, Wakayama-ken, Japan, 641

[21] Appl. No.: 640,695

[22] Filed: May 1, 1996

[30] Foreign Application Priority Data

May 12, 1995 [JP] Japan ................................ 7-114571

[51] Int. Cl.[6] .................................................. A61B 17/52
[52] U.S. Cl. .................................................. 600/9; 600/15
[58] Field of Search .................... 600/9, 15; 428/692, 428/328, 329, 325, 900

[56] References Cited

U.S. PATENT DOCUMENTS

| | | | |
|---|---|---|---|
| 4,095,587 | 6/1978 | Ishikawa | 600/15 |
| 4,162,672 | 7/1979 | Yazaki | 600/15 |
| 4,843,738 | 7/1989 | Masuda | 36/44 |
| 5,217,542 | 6/1993 | Nakamura et al. | 148/105 |

FOREIGN PATENT DOCUMENTS

| | | |
|---|---|---|
| 5676960 | 6/1981 | Japan . |
| 5103842 | 4/1993 | Japan ................................ 600/15 |

*Primary Examiner*—John P. Lacyk
*Assistant Examiner*—Rosiland Kearney
*Attorney, Agent, or Firm*—Wenderoth, Lind, & Ponack L.L.P.

[57] ABSTRACT

A sheet of fabric comprises a layer of magnetic powder, layer through applying or printing a power of magnetic material, in which the magnetic layer is composed of a mixture of a Sm2Co17 alloy and a binder, which comprises an antioxidant and an adhesive, coated over the fabric 1 by printing.

In use, the magnetic therapeutic sheet is cut into pieces of a desired size.

The magnetic therapeutic sheet may be applied to underwear including a shirt, socks, a corset, and a cloth covering a part of a human body.

8 Claims, 2 Drawing Sheets

MAGNETIC THERAPEUTIC SHEET AND A METHOD OF MAKING THE SAME

BACKGROUND OF THE INVENTION

The present invention relates to a method of making a magnetic therapeutic sheet for relieving lumbar pain, nervous pain such as stiff shoulder, muscular pain, and other inflammation.

1. Field of the Invention

A prior art therapeutic sheet or compress comprises commonly a stretchable fabric coated at one side with a film of adhesive material which contains a given amount of analgesic, antiphlogistic agent. The compress is used to cover an affected area with its adhesive side by directly applying to or securing with pieces of adhesive tape.

2. Description of Related Art

It is also known that magnetic flux helps ease lumbar or shoulder pain. For this end, a disk shaped magnet, for example, 5 mm in diameter and 2 mm in thickness, is provided for placing over the affected area with a strip of adhesive tape. More commonly, a base material such as a sheet of fabric is impregnated with grains or powder of magnet as well as an adhesive agent. This application will however be disadvantageous because the magnetic powder is located at the same area as of the adhesive agent and fails to provide an intensive magnetic effect to a desired area. As the magnetic powder is distributed throughout the base material and mixed with the adhesive agent, its magnetic force is reduced at each local region thus assuring less therapeutic effects.

We have developed and proposed a number of modified magnetic therapeutic sheets capable of providing both a wet pad effect and a magnetic therapeutic effect while ensuring the magnetic effect over a wider area, as disclosed in Japanese Patent Applications 3-95152(1991) 3-95153 (1991), 5-41011(1993), and 6-41011(1994).

Particularly, Application 5-41011 explains a method of making the magnetic layer through applying or printing a powder of magnetic material.

The magnetic powder is preferably a cobalt material ($Sm_2Co_{17}$, samarium cobalt) coated or printed on a sheet of fabric in the form of a magnetic layer which can provide a higher magnetic therapeutic effect.

There is however a problem that a component of cobalt in the magnetic powder is susceptible to oxidation when samarium cobalt is mixed with water and glue (referred to as a binder) for ease of application or printing on the fabric sheet.

If the samarium cobalt is stored in a sealed condition, water may be deoxidized releasing hydrogen which causes explosion or steam eruption.

The samarium cobalt, $Sm_2Co_{17}$, is a cobalt alloy containing 20 to 25% by weight of Sm, 10 to 20% by weight of Fe, 3 to 10% by weight of Cu, and 1 to 5% by weight of Zr. The cobalt alloy has a higher magnetic characteristic but is unfavorable for being plasticized. It is common that the cobalt alloy is milled to grains of about 500 micrometers for use as a magnetic material. This increases the entire surface of the material and will accelerate the oxidation when mixed with water.

Since the samarium cobalt tends to decline the magnetic characteristic when oxidized, its oxidation will be a serious drawback to be tackled.

If oil is substituted for the water in order to prevent the oxidation, its higher viscosity may cause clogging in an application or printing device and block the mesh of a fabric sheet lowering the air permeability.

Also, the surface of each grain of the magnetic material may be covered with a film of gold. However, this will dramatically increase the overall cost while preventing the oxidation.

It is an object of the present invention, in view of the foregoing predicaments, to provide a method of making a low-cost magnetic therapeutic sheet which is less susceptible to corrosion of cobalt components.

SUMMARY OF THE INVENTION

In accordance with the above, it is an object of this invention is to provide a magnetic therapeutic sheet having a layer of magnetic powder bonded directly to one side of a sheet of fabric. The magnetic powder layer comprises a mixture of a powder magnetic material and a deoxidizer.

Another object of this invention is to provide a method of making a magnetic therapeutic sheet which has a layer of magnetic powder bonded directly to one side of a sheet of fabric. This method is characterized in that the magnetic powder layer is bonded closely to the fabric sheet by printing or applying a mixture of a powder magnetic material and a deoxidizer over the fabric sheet.

The magnetic layer may be bonded closely to the fabric by printing or applying the deoxidizer over the fabric and then coating it with the magnetic powder.

The magnetic layer may further be covered with an adhesive layer.

The magnetic therapeutic sheet according to the present invention allows the magnetic layer to be composed of the mixture of the powder magnetic material and the deoxidizer (or anti-rust agent) and bonded to at least one side of the fabric, whereby the powder magnetic material will be prevented from oxidation or rusting with water while requiring no gold plating process. Thus, its magnetic characteristic will hardly be declined and remain consistent for a considerable period of time.

The method of making the magnetic therapeutic sheet according to the present invention comprises bonding the magnetic layer of powder magnetic material to one side of the fabric by common printing or application technique. This allows the finished magnetic therapeutic sheet to be low in price and have its magnetic layer resistive to oxidation. As the magnetic layer is deposited by the printing, it may be arranged in a desired pattern or a configuration corresponding to the affected area of a patient.

It is also possible for preventing oxidation of the magnetic layer to print or apply the deoxidizer over the fabric and then coat it with the powder magnetic material.

DETAILED DESCRIPTION OF THE PREFERRED EMBODIMENTS

A magnetic therapeutic sheet and a method of making the same according to the present invention will be described referring to the accompanying drawings.

Figure 1:
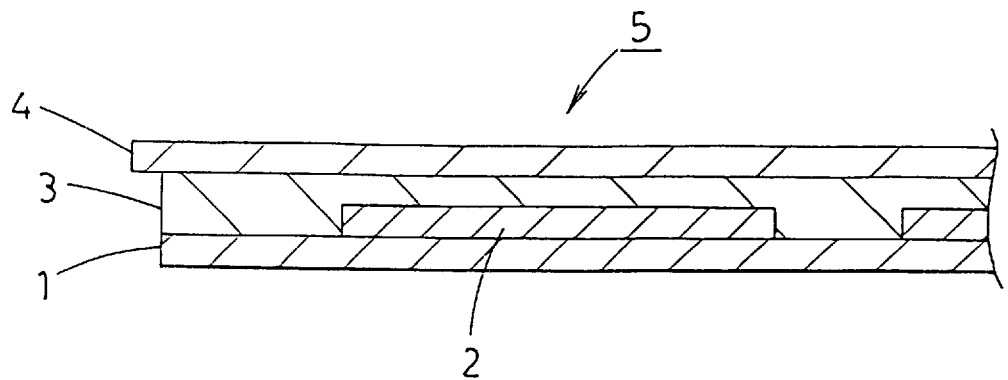
FIG. 1 is a cross sectional view showing an embodiment of a magnetic therapeutic sheet produced by a method according to the present invention.

FIG. 1 is a cross sectional view of the magnetic therapeutic sheet.

As shown, there are a base or fabric 1, a magnetic layer 2, an adhesive layer 3, and a polyethylene sheet 4.

The fabric 1 is preferably but not limited to a stretchable nonwoven fabric and may be selected from other appropriate sheet materials. The magnetic layer 2 is composed of a mixture of a Sm2Co17 alloy and a binder, which comprises an antioxidant and an adhesive, coated over the fabric 1 by printing. The antioxidant may be any agent, e.g. silicon, capable of preventing the oxidation of cobalt components. More particularly, the antioxidant may arbitrarily be selected from: sulfide such as terpene sulfide, alkylphenol sulfide, or calcium salt; phosphoric compound such as tributyl phosiphite or triphenyl phosphate; sulfur-phosphorus compound such as dithiophosphite; and metallic inactivator such as pinene, polybutene, dialkyl selenide, or phenothiazine.

The adhesive layer 3 is composed of an adhesive material such as natural rubber or zinc oxide resin and may preferably be mixed with, for example, a medical agent containing sodium polyacrylate, sorbitol, propylene glycol, and gelatine, or an analgesic, antiphlogistic agent including 0.5 g of 1-menthol, 1.0 g of dl-camphor, and 0.5 g of peppermint oil. It is also possible to add the medical agent to the magnetic layer 2.

The binder may be added with germanium for producing ion and/or a ceramic material for emitting far-infrared ray.

The polyethylene sheet 4 is provided for preventing drying of the adhesive layer 3 with the medical agent.

The magnetic layer 2 is printed by a common printing manner in which printing ink is replaced with the mixture of magnetic powder and adhesive.

After the magnetic therapeutic sheet 5 is completed, it is exposed to a field of intensive magnetic flux for having more than 0.5 gauss of the magnetic layer 2.

In use, the magnetic therapeutic sheet 5 is cut into pieces of a desired size. When its polyethylene sheet 4 have been removed, the piece is applied to the affected area. While the piece of the magnetic therapeutic sheet 2 being securely bonded with its adhesive layer 3 to the affected area, the magnetic force of more than 0.5 gauss from its magnetic layer 2 and the analgesic, antiphlogistic agent in the adhesive layer 3 act directly on a painful region under the skin giving simultaneously both analgesic and antiphlogistic effects.

The fabric 1 is highly stretchable and may hardly be peeled off while placed on a joint or moving part.

The cobalt powder in the magnetic layer 2 is protected by the deoxidizer and remains free from oxidation for a considerable length of time, producing a consistent magnetic field.

The magnetic therapeutic sheet 5 of the embodiment involves none of the costly gold plating process and will be fabricated by known economical steps.

Also, the magnetic layer 2 with the cobalt powder is formed over the fabric 1 by the conventional printing technique which contributes to the reduction of the overall cost.

The magnetic layer 2 may be printed in the form of multiple fragments or a desired shape. A group of the fragments can be applied at efficiency to the affected area of any size or shape.

The magnetic layer 2 may be implemented by applying or printing a film of the adhesive and then coating it with a mixture of the magnetic powder and the deoxidizer.

The magnetic layer 2 may be implemented by applying or printing a film of the deoxidizer and then coating it with the magnetic powder.

The magnetic layer 2 may be accompanied with a large number of extra magnetic grains dispersed thereover to increase the magnetic force.

The magnetic layer 2 is not limited to the prescribed constructions but may contain any other medical or adhesive agent so long as it provides a given intensity of magnetic force.

The fabric 1 may be coated at both sides with magnetic layers and adhesive layers. The magnetic layer 2 may be applied by spraying as compared to printing.

The magnetic layer 2 may be protected with an anti-rust coating which is substituted for the deoxidizer.

Figure 2:
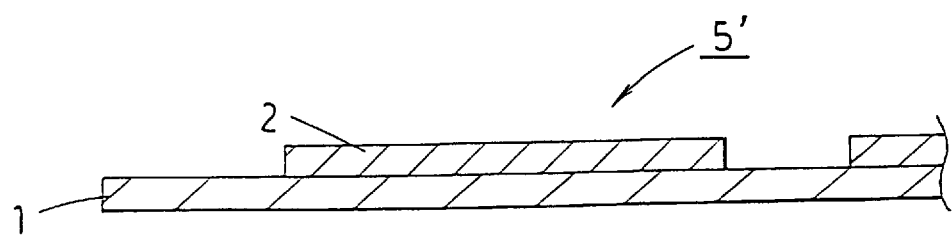
FIG. 2 is a cross sectional view of another embodiment of the magnetic therapeutic sheet according to the present invention.

Referring to FIG. 2, another magnetic therapeutic sheet 5' is arranged in which the magnetic layer 2 is formed directly over the fabric 1 without using any adhesive layer. In particular, the magnetic therapeutic sheet 5' may be used for making a garment design or other application.

Figure 3:
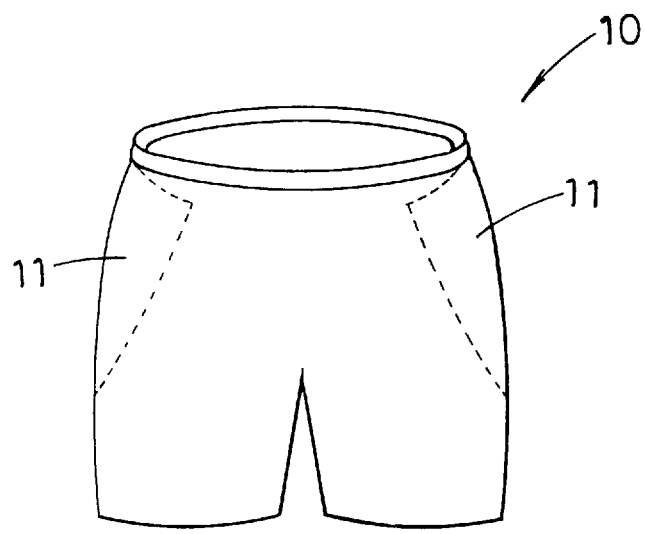
FIG. 3 is a perspective view of an underwear garment made of the magnetic therapeutic sheet of the present invention.
Figure 3:
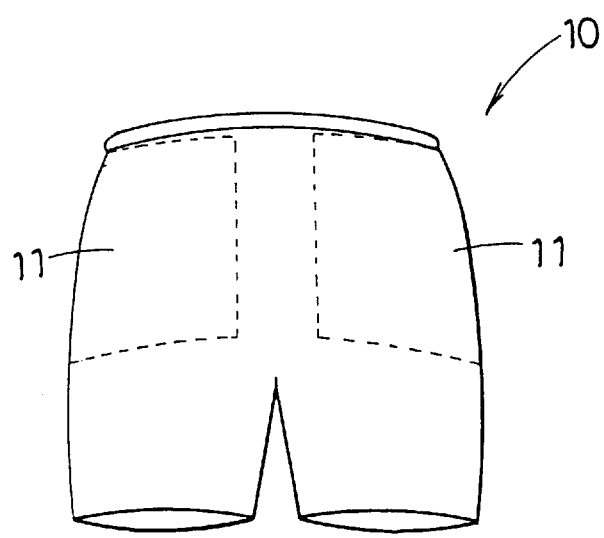

FIG. 3 is a perspective view showing an underwear (pants) 10 made of the magnetic therapeutic sheet of the present invention, viewed from upper front and lower back. The regions 11 defined by the dotted lines are associated with the magnetic layers 2 impregnated with the deoxidizer. It is true that the regions 11 carry none of the adhesive layers and the polyethylene sheets.

As understood, the regions 11 are located to cover the entire gluteus medius muscle or a lumbar muscle region of a human body where their magnetic therapeutic effects are concentrated. The magnetic layer 2 in each region 11 may be printed on either of the front and back sides of the underwear 10. It is also a good idea to have the magnetic layer 2 printed in a color(s) or in a desired design pattern.

This embodiment is not limited to the underwear but may be applied to any other garments including a shirt, socks, a corset, and a cloth covering a part of a human body.

What is claimed is:

1. A magnetic therapeutic sheet comprising a layer of magnetic powder bonded directly to at least one side of a sheet of fabric, the layer of magnetic powder comprising a mixture of a powder magnetic material, a deoxidizer and a germanium compound.

2. The magnetic therapeutic sheet as claimed in claim 1, wherein the sheet is included in a hip-covering region of an underwear.

3. A method of making the magnetic therapeutic sheet of claim 1, which comprises:

bonding the layer of magnetic powder to at least one side of the sheet of fabric;

printing or applying the deoxidizer over the sheet of fabric; and coating the sheet of fabric with the powder magnetic material.

4. A method of making the magnetic therapeutic sheet of claim 1, which comprises:

bonding the layer of magnetic powder to at least one side of the sheet of fabric;

mixing the powder magnetic material and the deoxidizer; and printing and applying the mixture of powder magnetic material and deoxidizer over the sheet of fabric.

5. A magnetic therapeutic sheet comprising a layer of magnetic powder bonded directly to at least one side of a sheet of fabric, the layer of magnetic powder comprising a mixture of a powder magnetic material, a deoxidizer and a ceramic material for emitting far-infrared ray.

6. The magnetic therapeutic sheet as claimed in claim 5, wherein the sheet is included in a hip-covering region of an underwear.

7. A method of making the magnetic therapeutic sheet of claim 5, which comprises:
   bonding the layer of magnetic powder to at least one side of the sheet of fabric;
   printing or applying the deoxidizer over the sheet of fabric; and
   coating the sheet of fabric with the powder magnetic material.

8. A method of making the magnetic therapeutic sheet of claim 5, which comprises:
   bonding the layer of magnetic powder to at least one side of the sheet of fabric;
   mixing the powder magnetic material and the deoxidizer; and
   printing and applying the mixture of powder magnetic material and deoxidizer over the sheet of fabric.

* * * * *